United States Patent [19]

Carver

[11] Patent Number: 4,652,757
[45] Date of Patent: Mar. 24, 1987

[54] METHOD AND APPARATUS FOR OPTICALLY DETERMINING DEFECTS IN A SEMICONDUCTOR MATERIAL

[75] Inventor: Gary E. Carver, Raritan Township, Hunterdon County, N.J.

[73] Assignee: AT&T Technologies, Inc., Berkeley Heights, N.J.

[21] Appl. No.: 762,086

[22] Filed: Aug. 2, 1985

[51] Int. Cl.$^4$ .................................. G01N 21/88
[52] U.S. Cl. ........................ 250/360.1; 250/338; 250/341; 250/358.1
[58] Field of Search ............... 250/360.1, 359.1, 358.1, 250/341, 340, 338 R, 572; 356/369, 237

[56] References Cited

U.S. PATENT DOCUMENTS

| | | | |
|---|---|---|---|
| 3,355,980 | 12/1967 | Mathias | 356/369 |
| 4,211,488 | 7/1980 | Kleinknecht | 356/369 |
| 4,352,016 | 9/1982 | Duffy et al. | 250/358.1 |
| 4,352,017 | 9/1982 | Duffy et al. | 250/358.1 |

OTHER PUBLICATIONS

Robert E. McMahon, "A Laser Scanner for Integrated Circuit Testing", Proceedings of the 10th Annual Conference on Reliability Physics, Las Vegas, Nevada (Apr. 1972) pp. 23–25.

I. Nagata, R. J. Galagali, S. Horiguchi, T. Sakai and T. Nakaya, "Optical Constants of Germanium Crystal Under Giant-Pulse Irradiation", *Journal of Physics D: Applied Physics*, vol. 3, No. 9 (Sep. 1970) pp. 1305–1313.

*Primary Examiner*—Janice A. Howell
*Assistant Examiner*—Constantine Hannaher
*Attorney, Agent, or Firm*—D. J. Kirk

[57] ABSTRACT

Individual defects in or near the surface of a silicon wafer (16) are detected by directing a time-modulated laser beam (44), having an energy level above the bandgap energy of the silicon material, towards the wafer. The beam (44) is focused to a one to two micron spot (48) on the wafer surface to photoexcite (i.e., pump) a high density of electrons and holes which changes the infrared reflectance in the area of the pumped spot. A probe beam (34) of infrared radiation is directed at the surface (0.126 square mm in area) of the substrate (16) and at a small angle thereto and the reflection thereof monitored by a detector (54). The pumped spot (48) is raster scanned within the area of the probe beam spot (38). The detector (54) detects only that portion of the intensity of reflected probe beam (34) that is modulated by the pump beam frequency to create a video display having a high spatial resolution showing individual defects.

8 Claims, 3 Drawing Figures

METHOD AND APPARATUS FOR OPTICALLY DETERMINING DEFECTS IN A SEMICONDUCTOR MATERIAL

TECHNICAL FIELD

The invention relates to testing the quality of semiconductor wafers. In particular, wafer defects are determined using non-destructive techniques.

BACKGROUND OF THE INVENTION

In the fabrication of semiconductor devices, the surface of the semiconductor material in which the devices are fabricated must be substantially free of both physical and crystalline defects. A high degree of crystalline perfection is necessary to produce reliable devices having good electrical properties. In order to control the properties of such devices, it is necessary to be able to determine the quality of semiconductor material that is being used to make the devices.

Defects in semiconductor material (e.g., silicon, InP, InGaAsP or the like) include dislocations, stacking faults, oxygen precipitates and heavy metal precipitates. Such defects, which are often one to two microns in size, have been detected using a variety of techniques including etch pit analysis, x-ray topography and electron beam induced current.

Etch pit analysis involves etching a silicon wafer and then viewing the pits that grow in the defective areas under an interference microscope. Individual stacking faults, dislocations and saucer pits can be distinguished after etching by the shape of the pits that each defect causes to grow. X-ray topography is accomplished by setting up an x-ray beam, the wafer and a film to catch Bragg-reflected rays. The relative angular positions of these three components are such that the Bragg law is satisfied when the beam strikes good material, but is not satisfied when it encounters defects. The film and sample are translated such that the reflected beam intensity for all points on the wafer are mapped onto the film. Spatial resolutions of 1–10 microns can be attained after 3 to 20 hours of exposure.

Electron beam induced current (EBIC) is accomplished inside a scanning electron microscope (SEM). The SEM beam is used to induce carriers within a sample, which are then separated by an electric field. The field is created by either a pn junction within the sample, a Schottky junction on the surface of the sample, or by mounting the sample within an external field. Contact to the sample is generally accomplished with silver paste or spring loaded fine wires. As the SEM beam is rastered in x-y plane the collected carriers provide intensity modulation of an x-y display. Carrier recombination at defects allows them to appear dark on the display screen, down to a spatial resolution of 0.5 micron. Although these techniques image defects with high spatial resolution in semiconductor material, they are either destructive, time consuming and/or require a vacuum.

One non-destructive optical technique for determining electrical non-uniformities in semiconductor wafers is described in U.S. Pat. No. 4,211,488 to Kleinknecht which issued on July 8, 1980. That patent makes use of the fact that crystalline imperfections or doping striations in a semiconductor wafer cause lower carrier lifetime and/or mobility during photoexcitation and therefore change the infrared reflectance of the material. The electrical non-uniformities or defective areas are detected by irradiating an area of the semiconductor wafer with a beam of monochromatic light having energy greater than the bandgap energy of the semiconductor wafer material. This will photoexcite (i.e., pump) a high density of electrons and holes which changes the infrared reflectance at the pumped area. The same surface area of the wafer is simultaneously irradiated with a second beam of monochromatic light having an energy less than the bandgap of the semiconductor material, whereby part of the second beam is reflected from the surface.

If the monitored area has moderate to low defect density and high carrier mobility, the reflectance of the surface will change during photoexcitation and the intensity of the reflected second beam will also change. However, if there is a high defect density within the area the reflectance of the surface will not change during photoexcitation and the intensity of the reflected second beam will remain unchanged. The intensity of the reflected beam is detected and the magnitude thereof is a measure of the carrier mobility and recombination time which is directly related to the density of the surface or near surface defects in the semiconductor material. The light beams in the Kleinknecht patent simultaneously illuminate an area of about 0.25 square mm.

Although such a technique can effectively provide information as to the average carrier lifetime and mobility over the 0.25 square mm area, it cannot resolve individual defects of one to two microns in size. There are two fundamental reasons for this fact. First, the laser providing the below-bandgap energy emits long wavelength light in the infrared part of the spectrum. Since basic diffraction theory predicts that minimum obtainable spot size is proportional to the f number times the wavelength, infrared light having wavelengths of interest for defect detection can be focused to spots no smaller than 10 to 20 microns. Second, the probe beam in the Kleinknecht patent has a high angle of incidence with respect to a normal to the wafer surface. This high angle leads to a further enlargement of the probe beam spot. Therefore, such a technique cannot focus the infrared beam to a small enough spot to resolve individual defects, of micron size, due to accepted basic optical theory. However, there is clearly great interest in resolving these micron-sized defects due to their influence on VLSI circuits having micron-sized features.

Accordingly, there is a need for a non-destructive defect detection system in which individual defects of one to two microns in size can be resolved.

SUMMARY OF THE INVENTION

The foregoing need is met with the instant method of detecting individual defects in or near the surface of a semiconductor, comprising: directing an infrared beam of monochromatic light, having an energy level below the bandgap energy of the semiconductor material, towards a first area of the semiconductor surface; simultaneously directing a time-modulated beam of monochromatic light, having an energy level above the bandgap energy of the semiconductor material, towards the surface of the semiconductor surface; focusing the time-modulated light beam to a second area, substantially smaller than, and within, the first area, the energy of the beam being substantially absorbed by said surface to excite electrons and holes in or near said material surface; detecting the intensity of the infrared light beam reflected from the semiconductor surface; and processing only that portion of the detected infrared beam intensity that is modulated at the frequency of the time-modulated light beam to locate individual defects in or near the semiconductor surface.

DETAILED DESCRIPTION

Figure 1:
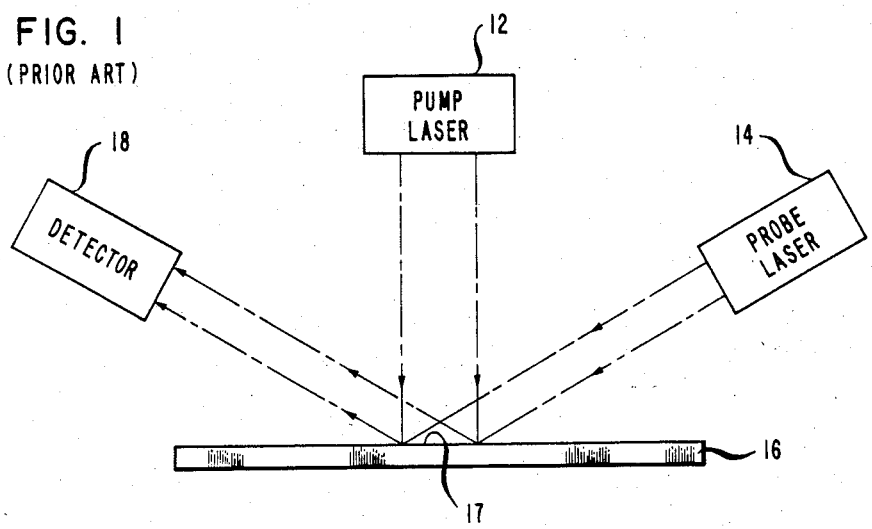
FIG. 1 is a schematic diagram of a known defect detection system.

FIG. 1 schematically depicts the known technique described in the aforementioned Kleinknecht patent which is incorporated by reference herein. A laser 12 modulated at 10 Hz and a laser 14 both direct light beams at a semiconductor substrate 16. The laser 12 outputs a pump beam that provides energy which is above the bandgap of the material of the substrate 16 while the laser 14 emits a beam that provides energy which is below the bandgap of the material of the substrate. The impingement on the substrate 16 of both laser beams is coincident in an area 17 which is approximately 0.25 square mm. If there are moderate to low defect densities in or near the surface of the substrate 16, the infrared reflectance of the surface changes and therefore the amount of reflected light from the laser 14 changes. However, if there are large defect densities in or near the substrate surface the reflectivity thereof is substantially unchanged during photoexcitation and the intensity of the reflected beam 14 will be substantially unchanged.

The beam from the laser 14 is reflected from the surface of the substrate 16 and impinges upon a detector 18 which measures its intensity. All of the intensity information is converted into electrical impulses which are forwarded to an oscilliscope (not shown) where the strength of the electrical signal is displayed in volts. As hereinbefore indicated, such a technique provides information as to the average carrier lifetime and mobility over a 0.25 square mm area but it cannot resolve individual defects of one to two microns in size.

Figure 2:
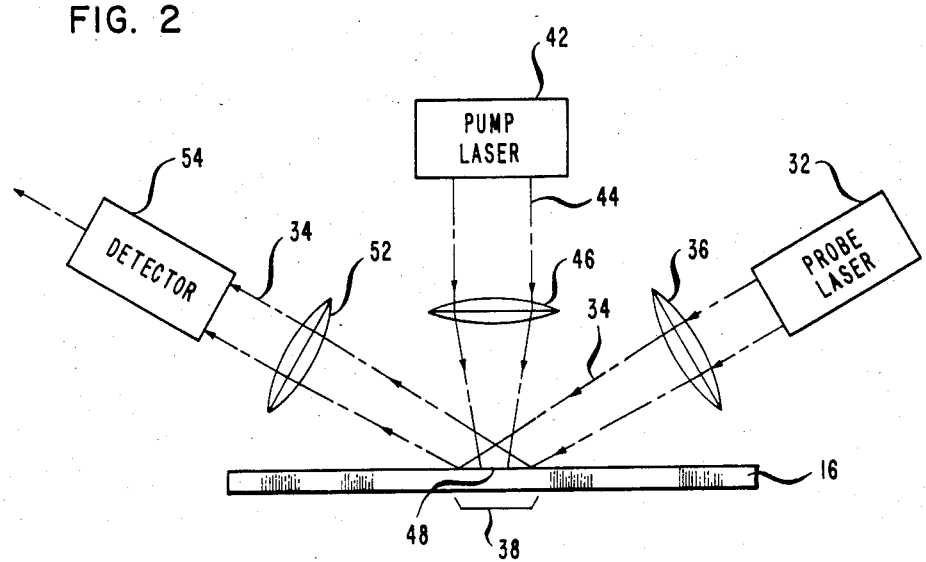
FIG. 2 is a schematic diagram of the instant defect detection system.

The instant technique, depicted by the schematic diagram in FIG. 2, overcomes the foregoing problem. A below-bandgap laser 32 directs a monochromatic probe beam 34 of infrared light (10.6 $\mu$m) towards a silicon substrate 16 and incident thereto at the Brewster angle. The probe beam 34 passes through a lens 36 which focuses the beam on the substrate 16. When the probe beam 34 has an incidence angle of 79° to a plane normal to the substrate 16 a probe spot 38 of approximately 0.126 square mm is formed on the substrate.

An above-bandgap laser 42 simultaneously directs a pump beam 44 towards the substrate 16. A lens 46 focuses the beam 44 to a small pump spot 48 of about 2 $\mu$m in diameter on the substrate 16. The focused pump beam 44 will alter the infrared reflectivity of the semiconductor material as hereinbefore described. The small pump spot 48 falls within the much larger probe spot 38. The relative size of the pump spot 48 and the probe spot 38 are not to scale in FIG. 2 but are shown in this manner for purposes of clarity of the drawings. Additionally, the pump beam 44 passes through an acoustic cell (not shown) to modulate the beam at 30 kHz in an exemplary embodiment.

The probe beam 34 is reflected from the surface of the substrate 16 and is relayed by a lens 52 for impingement upon a detector 54 where the reflected light intensity is converted to proportional electrical signals. The detector 54 and associated electronics process only those signals resulting from the reflected light from the probe beam 34 that is modulated at the 30 kHz frequency of the pump beam 44. As hereinbefore indicated the pump beam 44 will change the infrared reflectivity of the surface of the substrate 16 in the absence of defects but the infrared reflectivity is left substantially unchanged when the pump spot falls on a defect. Accordingly, that portion of the probe beam 34 impinging on the pump spot 48 will be modulated at the 30 kHz frequency of the pump beam 44 which alters the surface reflectivity at that frequency.

Additionally, the modulated pump beam 44 may be raster scanned within the 0.126 square mm spot of the probe beam 34 by selectively moving the pump beam and/or the substrate 16 in a well known manner. Once the probe spot 38 is fully scanned by the pump spot 48, it may then be moved to another location on the wafer 16 and the pump beam spot 48 again raster scanned therein. This process can be repeated until the full surface of the wafer 16 has been scanned and the reflections detected and forwarded to a video apparatus (not shown) for visual display.

Figure 3:
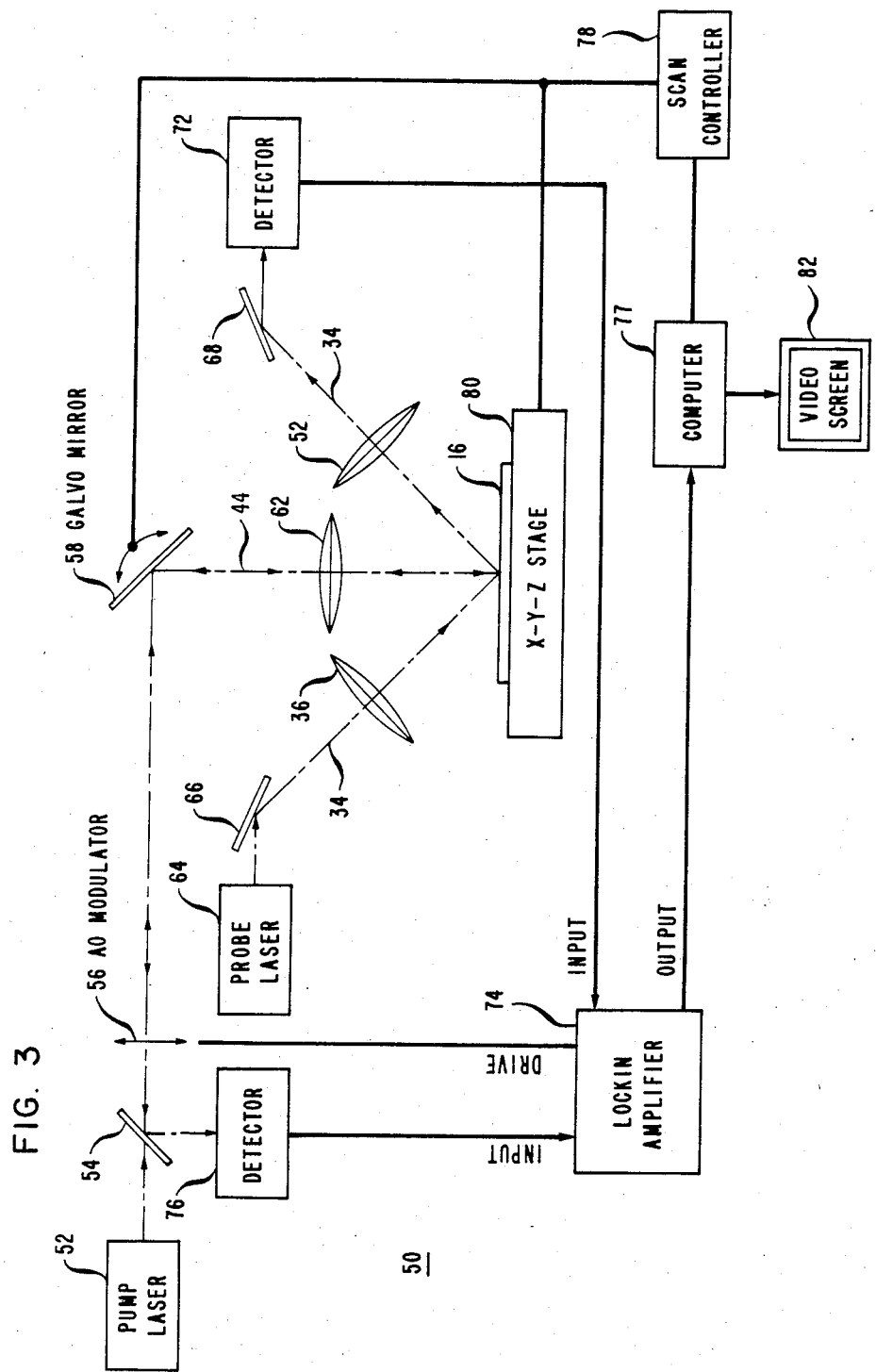
FIG. 3 is a block diagram of the instant defect detection system.

FIG. 3 is a block diagram of exemplary optics and electronics of the instant defect detection system 50. A 300 mw water cooled argon pumping laser 52, having a wavelength of 0.488 $\mu$m, is directed towards the silicon substrate 16 via a beamsplitter 54, an acoustic optical (AO) modulator 56 which time modulates the beam 44 at 30 kHz, a galvanometer mirror 58 and focusing optics 62. About 30 mw of light power from the argon pumping laser 52 actually impinges on the surface of the wafer 16, which is a sub-damage intensity density. About 1.5 watts from a five-watt, air-cooled $CO_2$ probe laser 64 is directed to the same location on the substrate 16 by reflecting the beam 34 from a fixed mirror 66 and through a focusing lens 36 to form an angle of incidence of 79° with a plane normal to the substrate. The probe beam 34 is reflected from the surface of the wafer 16 and further reflected from a fixed mirror 68 onto a HgCdTe detector 72 which has an output connected to an input of a lockin amplifier 74. The detector 72 and the lockin amplifier 74 process only that portion of the intensity of the reflected probe beam 34 that is modulated at the 30 kHz frequency. Advantageously, such a technique transforms the spot size typical for visible radiation of the pump beam 44 into the longer infrared radiation of the probe beam 34.

A light detector 76 monitors the position of the pump laser beam 44 by detecting reflections from the beamsplitter 54 and forwarding that information to the input of the lockin amplifier 74. A signal from the drive connection of the lockin amplifier 74 is forwarded to the acoustic optical modulator 56 to modulate the pump beam 44 at the same frequency as that at which the inputs of the lockin amplifier 74 are adjusted to receive. The output of the lockin amplifier 74 is sent to a computer 77 having outputs to a scan controller 78 and a video display 82. The output of the scan controller 78 is connected to a movable table 80 and the galvanometer controlled mirror 58 to control the relative positions of the table and the mirror 58.

The substrate 16 is mounted on a quartz vacuum chuck (not shown) which is supported on the movable table 80 which is capable of movement in the X, Y, Z and θ directions. The Z stage is used to bring the substrate 16 into focus. The focused position in the Z direction may change from one scan location to another due to the depth of focus of the lens used. The Y and θ stages are used to access various points on the surface of the wafer 16. The X stage and rotatable galvanometer mirror 58 are used to generate the raster scan in a well known fashion at approximately a thirty second frame rate. All four stages and the galvanometer mirror 58 operate under the control of the computer 77.

It is to be understood that the embodiments described herein are merely illustrative of the principles of the invention. Various modifications may be made thereto by persons skilled in the art which may embody the principles of the invention and fall within the spirit and scope thereof.

What is claimed is:

1. A method of detecting individual defects in or near the surface of a semiconductor material, comprising the steps of:
   directing an infrared beam of monochromatic light, having an energy level below the bandgap energy of the semiconductor material, towards a first area of the semiconductor surface;
   simultaneously directing a time-modulated beam of monochromatic light, having an energy level above the bandgap energy of the semiconductor material, towards the surface of the semiconductor;
   focusing the time-modulated light beam to a second area, substantially smaller than, and within, the first area, the energy of the beam being substantially absorbed by said surface to excite electrons and holes in or near said material surface to alter the reflectivity of said surface;
   detecting the intensity of the infrared light beam reflected from the semiconductor surface; and
   processing only that portion of the detected infrared beam intensity that is modulated at the frequency of the time-modulated light beam to locate defects in or near the semiconductor surface.

2. The method as set forth in claim 1, comprising the steps of:
   raster scanning the time modulated light beam to move the second area within the first area; and
   detecting the intensity of the light from only the infrared beam reflected from the surface at the modulated frequency.

3. The method as set forth in claim 1, wherein:
   the first area is approximately 0.126 square mm; and
   the second area is a spot of approximately 1 to 2 microns in diameter.

4. The method as set forth in claim 1, wherein:
   the semiconductor material is silicon.

5. The method as set forth in claim 1, wherein:
   the semiconductor material is InP.

6. The method as set forth in claim 1, wherein:
   the semiconductor material is InGaAsP.

7. The method as set forth in claim 1, wherein;
   the infrared beam has an angle of incidence to the semiconductor surface of 79° to a plane normal to said surface.

8. The method as set forth in claim 1, wherein:
   the time-modulated beam was generated by an argon laser; and
   the infrared beam was generated by a $Co_2$ laser.

* * * * *